United States Patent
Kern et al.

(10) Patent No.: US 11,007,232 B2
(45) Date of Patent: *May 18, 2021

(54) USE OF NEURAL CELLS DERIVED FROM HUMAN PLURIPOTENT STEM CELLS FOR THE TREATMENT OF NEURODEGENERATIVE DISEASES

(71) Applicant: International Stem Cell Corporation, Carlsbad, CA (US)

(72) Inventors: Russell A. Kern, Carlsbad, CA (US); Rodolfo Gonzalez, Carlsbad, CA (US); Ibon Garitaonandia, Carlsbad, CA (US)

(73) Assignee: International Stem Cell Corporation, Carlsbad, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/056,480

(22) Filed: Aug. 6, 2018

(65) Prior Publication Data

US 2018/0339001 A1    Nov. 29, 2018

Related U.S. Application Data

(63) Continuation of application No. 14/181,285, filed on Feb. 14, 2014, now Pat. No. 10,039,794.

(60) Provisional application No. 61/765,200, filed on Feb. 15, 2013.

(51) Int. Cl.
    *C12N 5/0797* (2010.01)
    *A61K 35/545* (2015.01)
    *A61K 35/30* (2015.01)
    *C12N 5/074* (2010.01)

(52) U.S. Cl.
    CPC ............ *A61K 35/545* (2013.01); *A61K 35/30* (2013.01); *C12N 5/0623* (2013.01); *C12N 5/0696* (2013.01); *C12N 2501/155* (2013.01); *C12N 2501/727* (2013.01); *C12N 2506/02* (2013.01); *C12N 2506/45* (2013.01)

(58) Field of Classification Search
    CPC .............. C12N 2506/02; C12N 5/0606; C12N 2501/16; C12N 2501/727; C12N 2501/999; C12N 5/0619; C12N 2506/04; C12N 5/0696; C12N 5/0623; C12N 2501/155; C12N 2506/45; A61K 35/545; A61K 35/30; A61K 35/54; A61P 25/28; A61P 25/16; A61P 25/14; A61P 25/00
    See application file for complete search history.

(56) References Cited

U.S. PATENT DOCUMENTS

| 5,453,357 | A | 9/1995 | Hogan |
| 5,670,372 | A | 9/1997 | Hogan |
| 5,690,926 | A | 11/1997 | Hogan |
| 5,843,780 | A | 12/1998 | Thomson |
| 6,200,806 | B1 | 3/2001 | Thomson |
| 6,251,671 | B1 | 6/2001 | Hogan et al. |
| 9,926,529 | B2 | 3/2018 | Gonzalez |
| 10,119,120 | B2 | 11/2018 | Takahashi et al. |
| 2006/0182724 | A1 | 8/2006 | Riordan |
| 2012/0010178 | A1 | 1/2012 | Rubin et al. |
| 2012/0142093 | A1 | 6/2012 | Takahashi et al. |

FOREIGN PATENT DOCUMENTS

| JP | 2011-519951 | | 7/2011 |
| JP | 2013-501502 | A | 1/2013 |
| JP | 2015-514437 | A | 5/2015 |
| WO | WO 2008/124142 | A1 * | 10/2008 |
| WO | 2012/112620 | A1 | 8/2012 |
| WO | WO 2013/163228 | A1 | 10/2013 |

OTHER PUBLICATIONS

Sperka et al., Nature Reviews, 13: 579-590, Sep. 2012.*
Janetka et al., Current Opinion in Drug Discovery and Development, 10(4):473-486, Jul. 2007.*
Neely et al., ACS Chemical Neuroscience, 3: 482-491, Mar. 2012.*
Zhu et al., Cell Stem Cell, 4:416-426, May 2009.
Zeng, Xianmin et al.: "Dopaminergic differentiation of human embryonic stem cells"; Stem Cells, Nov. 1, 2004, vol. 22, No. 6, pp. 925-940.
Yan, Xingrong et al: "Differentiation of neuron-like cells from mouse parthenogenetic embryonic stem cells"; Neural Regeneration Research, Feb. 5, 2013, XP055314130, 9 pages.
Supplementary European Search Report dated Nov. 28, 2016, regarding EP 14 75 1195.
Stewart, Zoe A., Matthew D. Westfall, and Jennifer A. Pietenpol. "Cell-cycle dysregulation and anticancer therapy." Trends in Pharmacological Sciences 24.3 (2003): 139-145. p. 142, col. 2, para 2.
Srivastava, Madhulika, and Narinder K. Kapoor. "Guggulsterone induced changes in the levels of biogenic monoamines and dopamine?—hydroxylase activity of rat tissues." Journal of Biosciences 10.1 (1986); 15-19. abstract, Table 1.
Semechkin et al.: "In Vivo Efficacy Study of Stem Cell Derived Neuronal Cells for the Treatment of Parkinson's Disease (S23. 007)"; Neurology, Feb. 12, 2013, vol. 80, No. 7, 3 pages.
Sanchez-Pernaute et al., Stem Cells, 23:914-922, 2005.
Sanchez-Pernaute et al., Brain, 131:2127-2139, 2008.
Revazova et al. Cloning and Stem Cells, vol. 9, No. 3: 432-449, 2007.
Redmond et al., PNAS, 104(29):12175-12180, Jul. 17, 2007.
Perrier, A. L. et al: "Derivation of midbrain dopamine neurons from human embryonic stem cells"; Proceedings of the National Academy of Sciences, Aug. 24, 2004, vol. 101, No. 34, pp. 12543-12548.
Neely et al. ACS Chem Neurosci, 3(6):482-491, Published online Mar. 5, 2012.

(Continued)

*Primary Examiner* — Kimberly Ballard
*Assistant Examiner* — Stacey N MacFarlane
(74) *Attorney, Agent, or Firm* — DLA Piper LLP (US)

(57) ABSTRACT

The present invention is based in part methods for treating neurodegenerative diseases and disorders. Specifically, the present invention disclose methods for treating neurodegenerative disorders suing neural stem cells (NSCs) and/or pluripotent stem cell (PSC) derived neurons or neuron precursor cells. The present invention also discloses methods to induce endogenous dopaminergic neurons to release dopamine and increase the levels of dopamine in a subject.

10 Claims, 7 Drawing Sheets

(56) References Cited

OTHER PUBLICATIONS

Kriks, Sonja et al.: "Dopamine neurons derived from human ES cells efficiently engraft in animal models of Parkinson's disease"; Nature, Nov. 6, 2011, XP55152305, ISSN: 0028-0836, DOI: 10.1038/nature10648, 7 pages.
Kirkeby et al., Cell Reports, 1:703-714, Jun. 2012.
Japanese Office Action dated Nov. 16, 2017 regarding JP 2015-558169.
Isaev, Dmitry A. el al.: "In vitro differentiation of human parthenogenetic stem cells into neural lineages"; Regenerative Medicine, Jan. 1, 2012, vol. 7, No. 1, pp. 37-45.
International Search Report and Written Opinion received for PCT Patent Application No. PCT/US2014/016600, dated May 23, 2014, 8 pages.
International Preliminary Report on Patentability received for PCT Patent Application No. PCT/US2014/016600, dated Aug. 27, 2015, 8 pages.
Gonzalez, Rodolfo et al.: "Denying dopaminergic neurons for clinical use. A practical approach"; Scientific Reports, Mar. 15, 2013, vol. 3, XP055209689, 5 pages.
Freed, C.R., et al: "Transplantation of Embryonic Dopamine Neurons for Severe Parkinson's Disease"; N Engl J Med, Mar. 8, 2001, vol. 344, No. 10, p. 710-719.
Freed et al., Neurotherapeutics 8:549-561, Oct. 15, 2011.
Buhnemann, C. et al.:"Neuronaldifferentiation of transplanted embryonic stem cell-derived precursors in stroke lesions of adult rats"; Brain, Jun. 9, 2006, vol. 129, No. 12, pp. 3238-3248.
Brederlau, Anke et al.: "Transplantation of Human Embryonic Stem Cell-Derived Cells to a Rat Model of Parkinson's Disease: Effect of In Vitro Differentiation on Graft Survival and Teratoma Formation"; Stem Cells, Jun. 1, 2006, vol. 24, No. 6, pp. 1433-1440.
Barberi et al., vol. 21 No. 10, Published online Sep. 21, 2003.
Ahmad, Ruhel et al.: "Functional Neuronal Cells Generated by Human Parthenogenetic Stem Cells"; PLOS ONE, Aug. 6, 2012, vol. 7, No. 8, E42800, pp. 1-10.
Lindvall, Ollie et al.: *"Evidence for Long-term Survival and Function of Dopaminergic Grafts in Progressive Parkinson's Disease"*; Annals of Neurology, Feb. 1994, vol. 35, No. 2, pp. 172-180.
Svendsen, Clive N. et al.: *"Long-Term Survival of Human Central Nervous System Progenitor Cells Transplanted into a Rat Model of Parkinson's Disease"*; Experimental Neurology, 1997, vol. 148, pp. 135-146.
Zhou, Jiaxi et al.: *"High-Efficiency Induction of Neural Conversion in hESCs and hiPSCs with a Single Chemical Inhibitor of TGF-13 Superfamily Receptors"*; Stem Cells, Oct. 2010; 28(10): 1741-1750. doi:10.1002/stem.504.

* cited by examiner

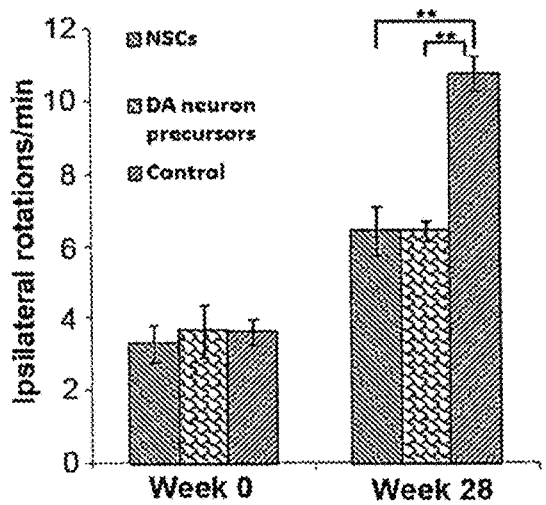
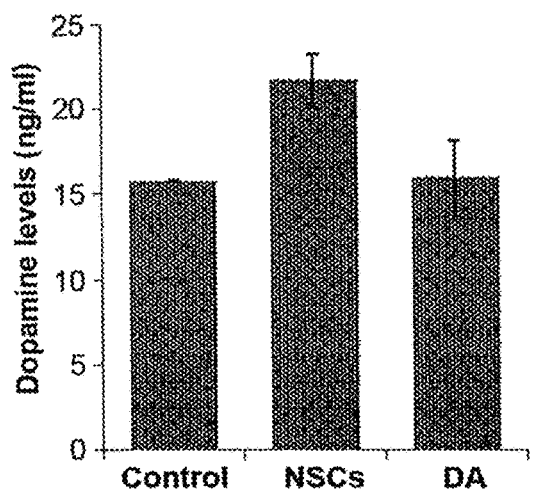
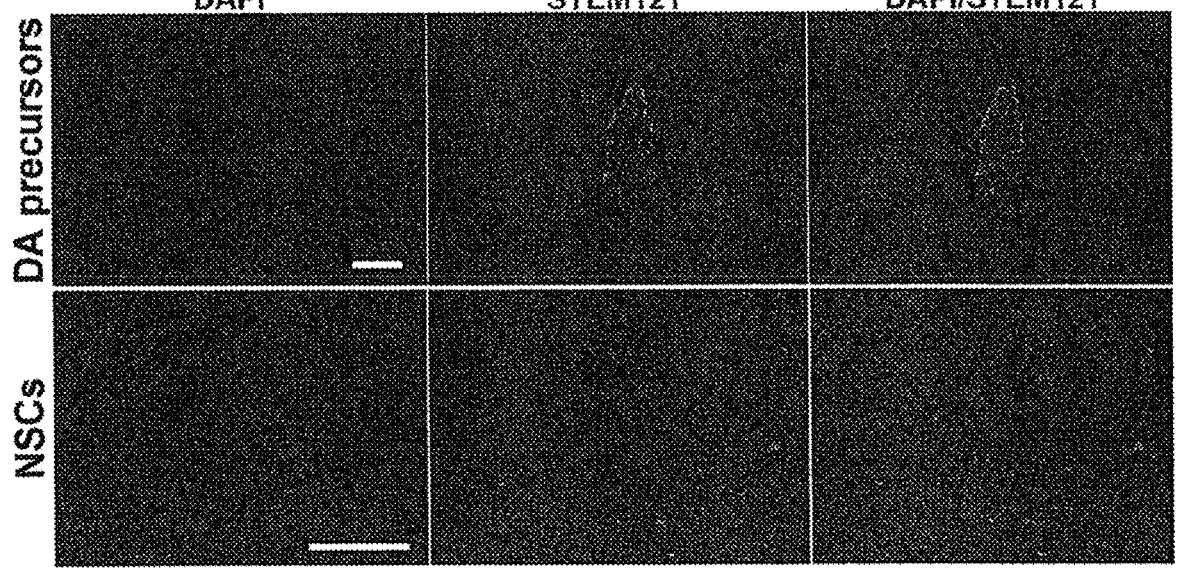
FIG. 3C
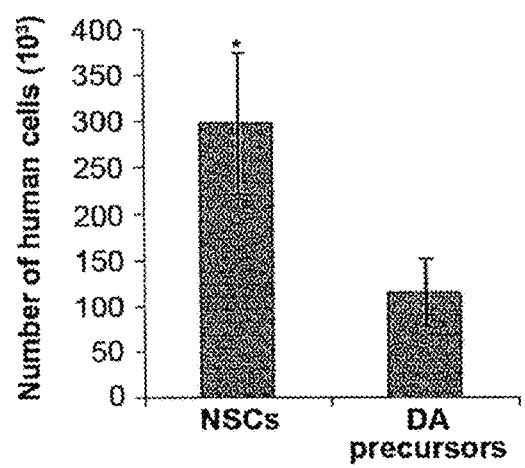
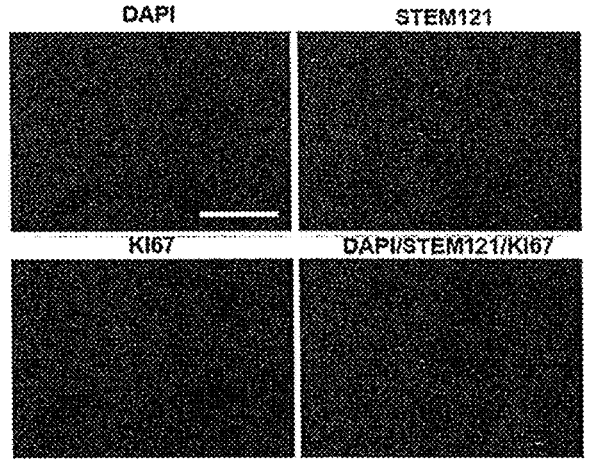
FIG. 3D  FIG. 3E

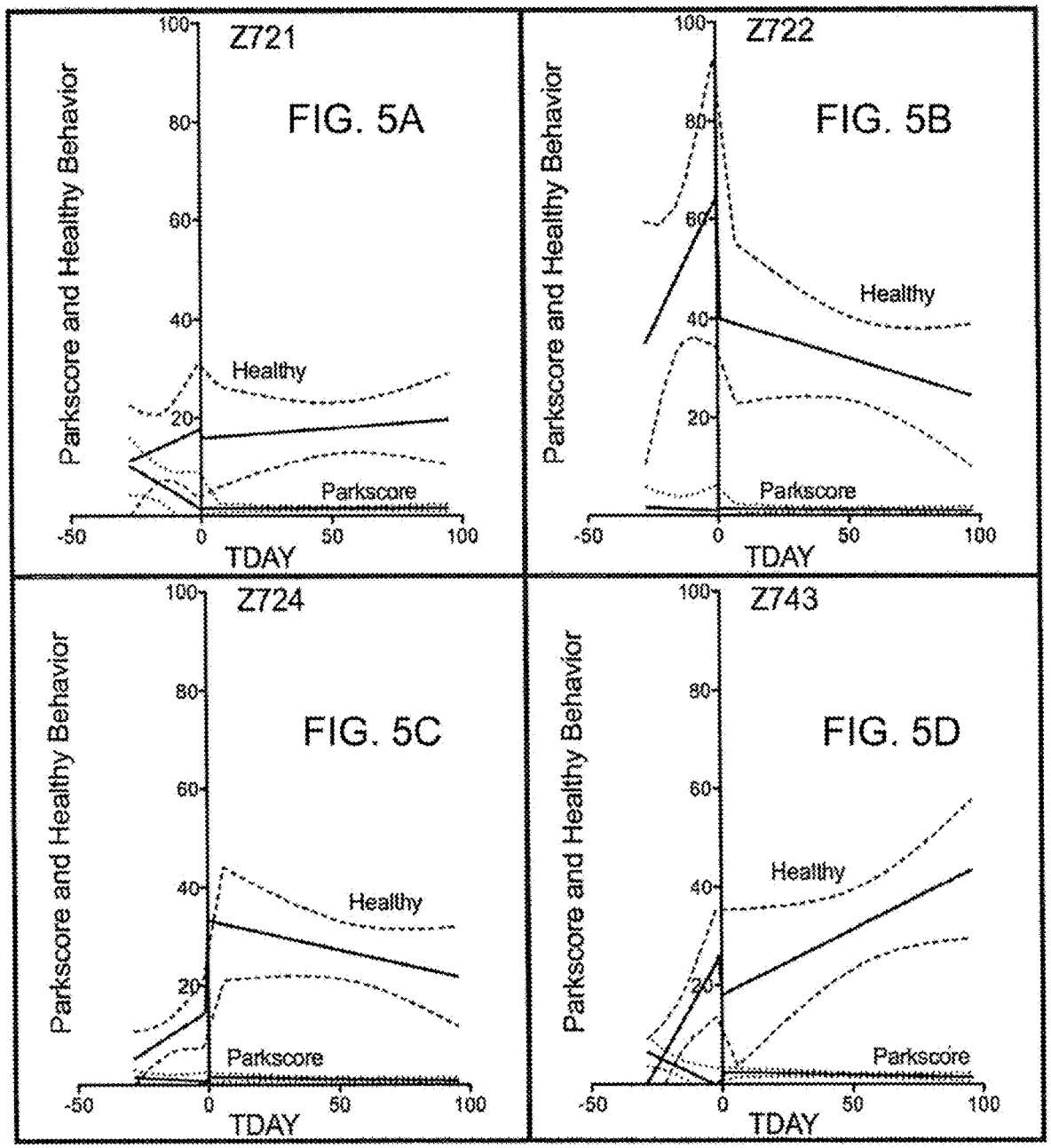

TH

DAPI/TH

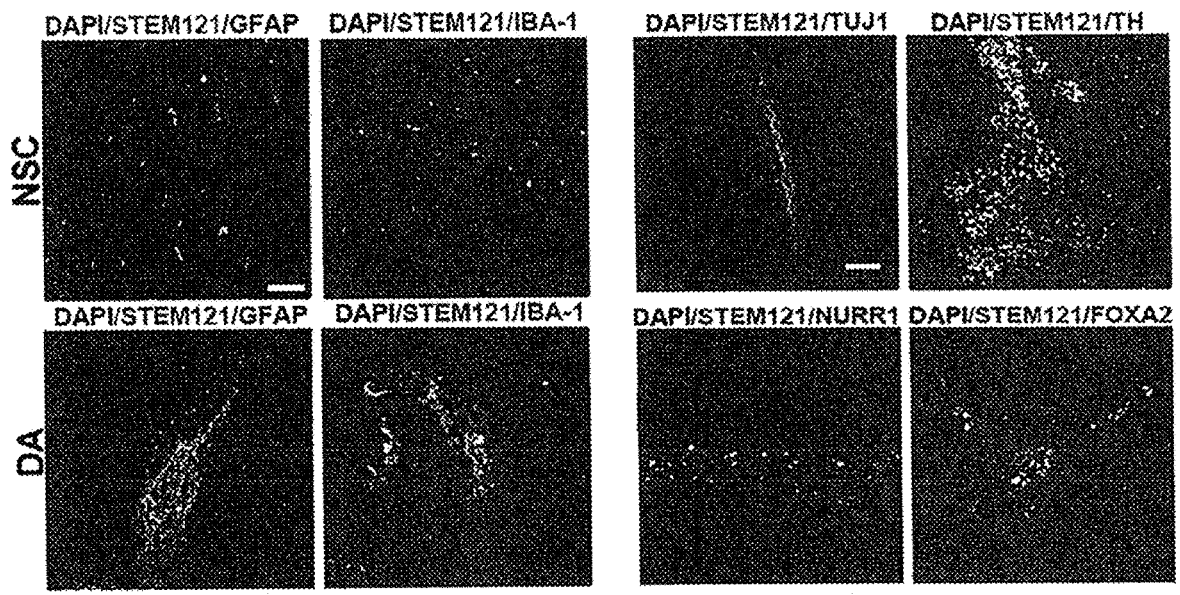
FIG. 7A
FIG. 7B
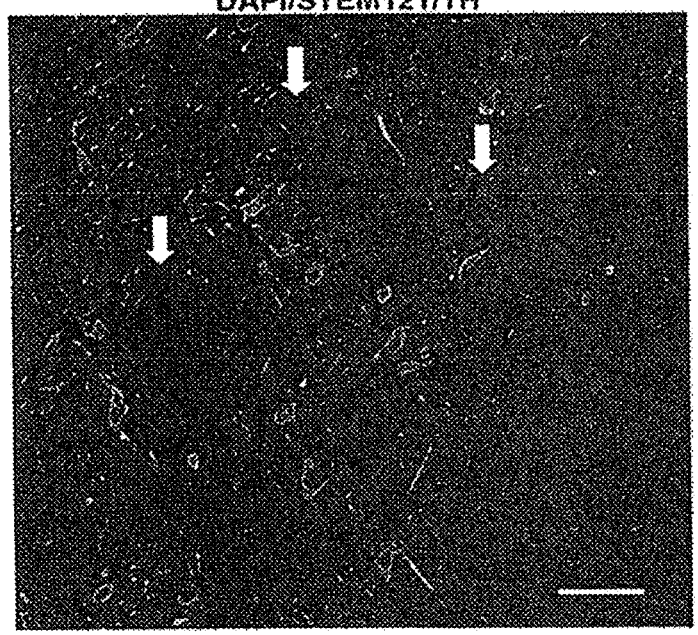
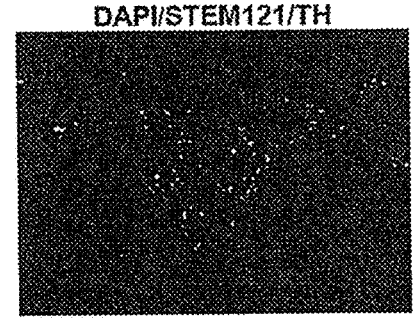
FIG. 7C
FIG. 7D
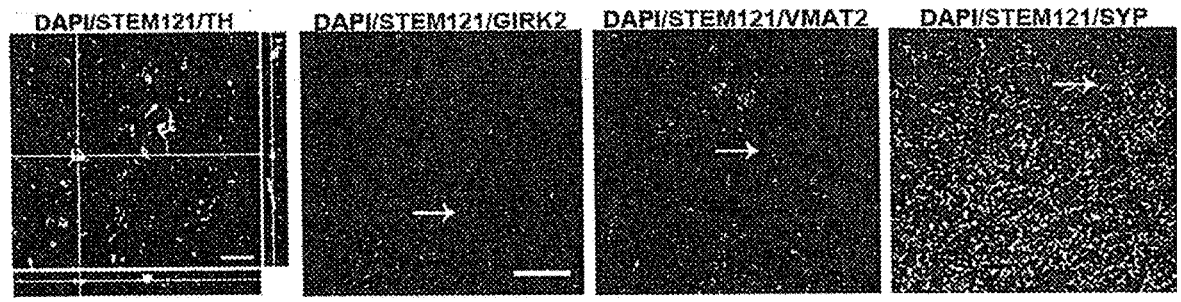
FIG. 7E

USE OF NEURAL CELLS DERIVED FROM HUMAN PLURIPOTENT STEM CELLS FOR THE TREATMENT OF NEURODEGENERATIVE DISEASES

CROSS REFERENCE TO RELATED APPLICATIONS

This application is a continuation application of U.S. application Ser. No. 14/181,285 filed Feb. 14, 2015, now issued as U.S. Pat. No. 10,039,794; which claims the benefit under § 119(e) to U.S. Application Ser. No. 61/765,200 filed Feb. 15, 2013. The disclosure of each of the prior applications is considered part of and is incorporated by reference in the disclosure of this application.

BACKGROUND OF THE INVENTION

Field of the Invention

The invention relates generally to the diagnosis, prognosis, progression, and treatment of neurodegenerative disorders or diseases. More specifically, the invention relates to the use of neural stem cells (NSCs) or pluripotent stem cell (PSC) derived neurons or neuron precursor cells for the treatment of neurodegenerative diseases.

Background Information

Human pluripotent stem cells (hPSCs) are cells that can differentiate into a large array of cell types. Stem cells are distinguished from other cell types by two important characteristics. First, they are unspecialized cells capable of renewing themselves through cell division, sometimes after long periods of inactivity. Second, under certain physiologic or experimental conditions, they can be induced to become tissue- or organ-specific cells with special functions. In some organs, such as the gut and bone marrow, stem cells regularly divide to repair and replace worn out or damaged tissues. In other organs, however, such as the pancreas and the heart, stem cells only divide under special conditions.

During embryonic development, stem cells form the tissues of the body from three major cell populations: ectoderm, mesoderm and definitive endoderm. Mesoderm gives rise to blood cells, endothelial cells, cardiac and skeletal muscle, and adipocytes. Definitive endoderm generates liver, pancreas and lung. Ectoderm gives rise to the nervous system, skin and adrenal tissues.

Stem cells have potential in many different areas of health and medical research. Some of the most serious medical conditions, such as cancer and birth defects, are due to problems that occur when cells undergo a transformation. Understanding normal cell development and differentiation mechanisms will allow for a better understanding of these conditions.

Another potential application of stem cells, is making cells and tissues for medical therapies. Today, donated organs and tissues are often used to replace those that are diseased or destroyed. Unfortunately, the number of people needing a transplant far exceeds the number of organs available for transplantation. Stem cells offer the possibility of a renewable source of replacement cells and tissues to treat a myriad of diseases, conditions, and disabilities including Parkinson's disease, amyotrophic lateral sclerosis, spinal cord injury, burns, heart disease, diabetes, and arthritis.

Neurodegenerative diseases are characterized by the progressive loss of neurons or the function of neurons. Common neurodegenerative diseases are Parkinson's, Alzheimer's, and Huntington's disease. For example, Parkinson's disease (PD) is a neurodegenerative disorder caused by a progressive degeneration of midbrain dopamine neurons in the substantia nigra pars compacta. There is currently no cure for PD and treatments such as deep brain stimulation and levodopa can alleviate some of the symptoms but loose efficacy over time. The localized nature of the loss of DA neurons in the substantia nigra offers the opportunity for cell replacement therapy by implanting neuronal cells, either neural stem cells (NSC) or neurons, differentiated from human pluripotent stem cells (hPSC) into the brain of PD patients.

SUMMARY OF THE INVENTION

The present invention is based in part the discovery that stem cell therapy is beneficial for the treatment of neurodegenerative disorders. Specifically, the present invention disclose methods for treating neurodegenerative disorders suing neural stem cells (NSCs) and/or pluripotent stem cell (PSC) derived neurons or neuron precursor cells. The present invention also discloses methods to induce endogenous dopaminergic neurons to release dopamine and increase the levels of dopamine in a subject.

In one embodiment, the present invention provides a method for treating a neurodegenerative disease or disorder comprising administering to a subject in need thereof, neural stem cells (NSCs) or pluripotent stem cell (PSC) derived neurons or neuron precursor cells, into the brain of the subject, thereby treating the disorder. In one aspect, the subject is human. In another aspect, the neural stem cells or the PSCs are human. In a further aspect, the PSCs are partially or fully differentiated prior to administration. In an additional embodiment, the PSCs are human embryonic stem cells (hESCs), human parthenogenetic stem cells (hpSCs) or induced pluripotent stem cells (iPSCs). In a preferred aspect, the PSCs are human parthenogenetic stem cells. In one aspect, the neurodegenerative disease or disorder is Alzheimer's Disease, Parkinson's Disease, Amyotrophic Lateral Sclerosis (ALS) or Huntington's Disease. In a specific aspect, the neurodegenerative disease or disorder is Parkinson's disease. In an additional aspect, the NSCs or PSC derived neuron precursor cells differentiate in vivo into dopaminergic neurons. In one aspect, the NSCs or PSC derived neurons or neuron precursor cells increase the levels of dopamine in the subject. In another aspect, the NSCs or PSC derived neurons or neuron precursor cells induce endogenous dopaminergic neurons to release dopamine. In a further aspect, the NSCs are derived by the method comprising obtaining human pluripotent stem cells (hPSCs); and treating the hPSCs with a checkpoint kinase 1 (CK1) inhibitor and a bone morphogenic protein (BMP) inhibitor. In one aspect, the pluripotent stem cell (PSC) derived neurons or neuron precursor cells are dopaminergic.

In an additional embodiment, the present invention provides a method of increasing dopamine levels in a subject comprising administering to a subject in need thereof, neural stem cells or pluripotent stem cell (PSC) derived neurons or neuron precursor cells, into the brain of the subject, thereby increasing dopamine levels.

In another embodiment, the present invention provides a method of inducing endogenous dopaminergic (DA) neurons to release dopamine comprising administering to a subject in need thereof, neural stem cells (NSCs) or pluripotent stem cell (PSC) derived neurons or neuron precursor cells, into the brain of the subject, thereby inducing the endogenous DA neurons to release dopamine.

In a further embodiment, the present invention provides a method of treating a subject with a neurodegenerative disease or disorder comprising: obtaining human pluripotent stem cells (hPSCs); treating the hPSCs with a checkpoint kinase 1 (CK1) inhibitor and a bone morphogenic protein (BMP) inhibitor; and administering the cells into the brain of the subject, thereby treating the neurodegenerative disorder. In one aspect, hPSCs are human embryonic stem cells (hESCs), human parthenogenetic stem cells (hpSCs) or induced pluripotent stem cells (iPSCs). In a preferred aspect, the hPSCs are obtained by parthenogenesis or nuclear transfer. In an additional aspect, the hPSCs are obtained by the method comprising: parthenogenetically activating a human oocyte, wherein activating comprises: contacting the oocyte with an ionophore at high $O_2$ tension and contacting the oocyte with a serine-threonine kinase inhibitor under low $O_2$ tension; cultivating the activated oocyte at low $O_2$ tension until blastocyst formation; transferring the blastocyst to a layer of feeder cells, and culturing the transferred blastocyst under high $O_2$ tension; mechanically isolating an inner cell mass (ICM) from trophectoderm of the blastocyst and culturing the cells of the ICM on a layer of feeder cells under high $O_2$ tension, thereby producing human stem cells. In one aspect, the CK1 inhibitor is SB2180708. In another aspect, the BMP inhibitor is Dorsomorphin, LD-193189 or DMH-1.

In one embodiment, the present invention provides a method of treating a subject with a neurodegenerative disease or disorder comprising: obtaining human pluripotent stem cells (hPSCs); treating the cells with a checkpoint kinase 1 (CK1) inhibitor and a bone morphogenic protein (BMP) inhibitor; treating the cells with guggulsterone; and administering the cells into the brain of the subject, thereby treating the neurodegenerative disorder.

BRIEF DESCRIPTION OF THE DRAWINGS

(FIG. 1A): Flow diagram of differentiation of hPSCs into NSCs and DA neuron precursor cells. (FIG. 1B, FIG. 1C): Immunofluorescence protein expression analysis of PAX6, Nestin and Musashi in NSCs (FIG. 1B), and NURR1, FOXA2, and TUJ1 in DA neuron precursor cells (FIG. 1C). Scale bars=100 µm.

(FIG. 2A): Gene expression analyses of NSCs, DA neuron precursor cells, and hPSCs by RT-PCR. (FIG. 2B): Heatmap showing differentially expressed genes between DA neuron precursor cells and NSCs.

FIGS. 3A-3E show behavior, biochemical and engraftment analysis of transplanted 6-OHDA lesioned rats. (FIG. 3A): Amphetamine-induced rotation analysis in 6-OHDA-lesioned rats transplanted with NSCs and DA neuron precursor cells. (FIG. 3B): Dopamine levels in rat brains transplanted with NSCs, DA neuron precursor cells, and sham control. (FIG. 3C): Engraftment and survival of NSC and DA neuron precursor cell grafts 28 weeks post-transplantation detected with human-specific marker (STEM121). (FIG. 3D): Number of human cells detected in rat brains transplanted with NSCs and DA neuron precursor cells. (FIG. 3E): Engrafted NSCs (STEM121) did not co-stain with proliferation marker Ki67. Scale bars=100 µm.

(FIG. 4A): Schematic showing migration of the engrafted NSCs to the substantia nigra. Sagittal plane shows relative distance between injection site in the striatum (red dot in coronal section) and substantia nigra (SN). (FIG. 4B): Glial scarring (GFAP) and increase in microglial numbers (IBA-1) against DA neuron precursor cell grafts (STEM121) in rats. (FIG. 4C): No glial scarring (GFAP) or IBA-1+ microglia were found surrounding the engrafted NSCs in rats. Scale bars=100 µm.

FIGS. 5A-5D show the behavior in transplanted MPTP treated non-human primates. Parkinson and Healthy scores of monkeys transplanted with NSCs [Z722 (FIG. 5A) and Z721 (FIG. 5B)] and DA neuron precursor cells [Z724 (FIG. 5C) and Z743 (FIG. 5D)]. The predicted values from a linear regression of "Healthy Behavior" and of "Parkinson's Score" are plotted (straight lines) before and after cell injections. Each of these has the 95% Confidence level plotted (curved lines) above and below the regression line.

(FIG. 6A-FIG. 6B): Biochemical analysis of dopamine levels (FIG. 6A), and HVA/DA ratios (FIG. 6B) of monkey's transplanted with NSC's and DA neuron precursor cells. (FIG. 6C-FIG. 6D) Immunohistochemistry analysis of striatal tissue (FIG. 6C), and substantia nigra (FIG. 6D) of monkeys transplanted with NSCs and DA neuron precursor cells stained for tyrosine hydroxylase (TH). Scale bars=1 cm for C and 100 µm for D.

FIGS. 7A-7E show the immune response and phenotype of transplanted cells in MPTP treated non-human primates. (FIG. 7A): Monkey brain tissue transplanted with NSCs or DA neuron precursor cells (STEM121) stained for astrocyte marker (GFAP) and microglial marker (IBA-1). (FIG. 7B): DA neuron precursor cell grafts (STEM121) stained for TUJ1, TH, NURR1, and FOXA2. (FIG. 7C): Engrafted NSCs (STEM121) appeared undifferentiated (Nestin) and were found along the nigrostriatal pathway (bottom panel). (FIG. 7D): Substantia nigra of NSC transplanted monkeys with white arrows pointing to human NSCs (STEM121) in close contact to host DA neuron precursor cells (TH). (FIG. 7E): A small proportion (~1%) of implanted NSCs differentiated into DA neuron precursor cells. Yellow lines and white arrows to human NSC derived neurons (STEM121) co-labeling with TH, GIRK2, VMAT2, and SYP. Scale bars=100 µm.

DETAILED DESCRIPTION OF THE INVENTION

Figure 1A:
FIGS. 1A-1C show derivation of NSCs and DA neuron precursors from hPSCs.
Figure 1B:
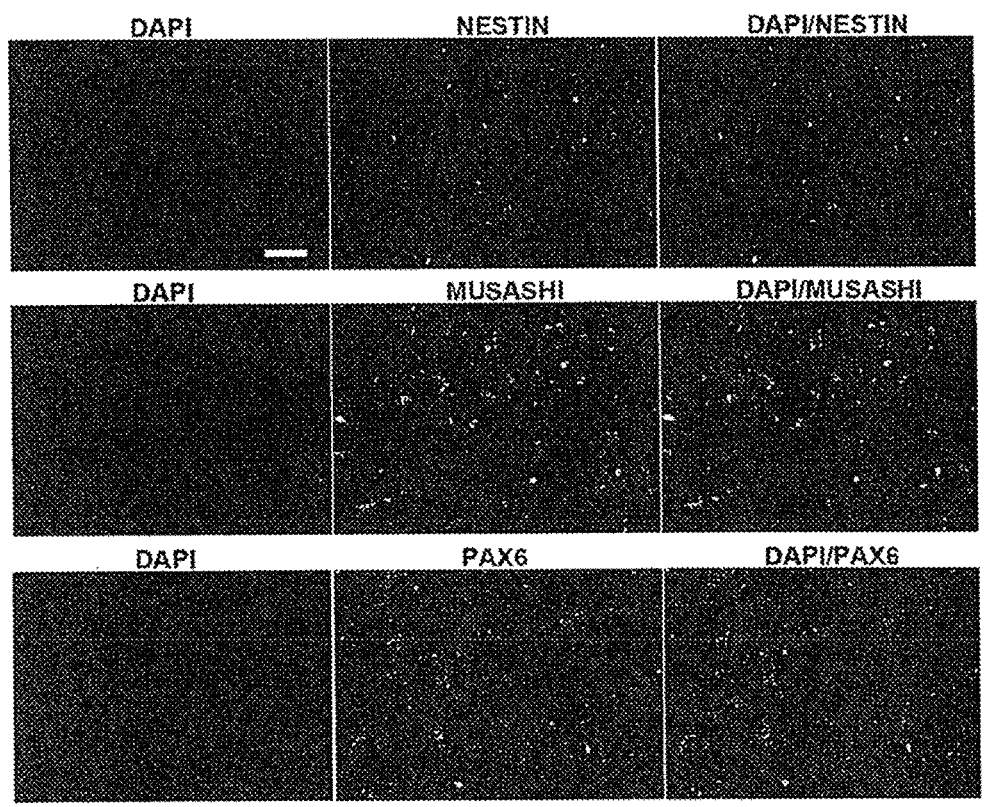
Figure 1C:
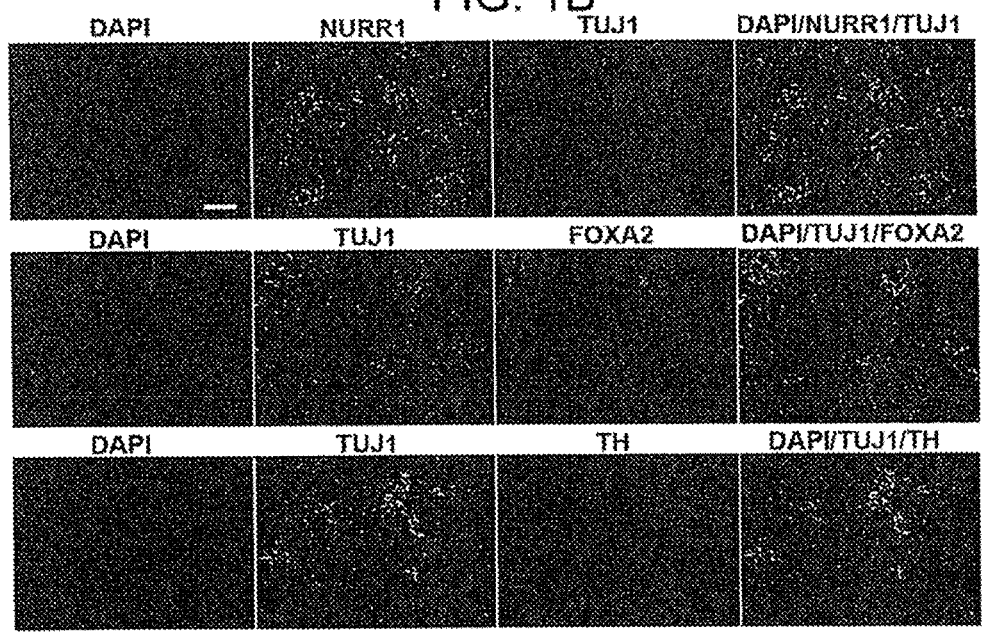

The present invention is based in part the discovery that stem cell therapy is beneficial for the treatment of neurodegenerative disorders. Specifically, the present invention disclose methods for treating neurodegenerative disorders suing neural stem cells (NSCs) and/or pluripotent stem cell (PSC) derived neurons or neuron precursor cells. The present invention also discloses methods to induce endogenous dopaminergic (DA) neurons to release dopamine and increase the levels of dopamine in a subject.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The present invention provides methods for the treatment of neurodegenerative disorders by administering neural stem cells (NSCs) pluripotent stem cell (PSC) derived neurons or neuron precursor cells.

NSCs may play a vital role in the treatment of neurological diseases and disorders. Neurodegeneration is the umbrella term for the progressive loss of structure or function of neurons, including death of neurons. Many neurodegenerative diseases including Parkinson's, Alzheimer's, and Huntington's occur as a result of neurodegenerative processes and are characterized by progressive nervous system dysfunction. Neurological diseases and disorders include, but are not limited to, Alzheimer's Disease and other dementias, Brain Cancer, Degenerative Nerve Diseases, Encephalitis, Epilepsy, Genetic Brain Disorders, Head and Brain Malformations, Hydrocephalus, Stroke, Parkinson's Disease, Multiple Sclerosis, Amyotrophic Lateral Sclerosis (ALS or Lou Gehrig's Disease), Huntington's Disease, Prion Diseases, stroke and others.

NSCs have been shown to engage in the migration and replacement of dying neurons. Additionally, the role of hippocampal stem cells during stroke in mice has been elucidated. These results demonstrated that NSCs can engage in the adult brain as a result of injury. Furthermore, if has been demonstrated that NSCs migrate to brain tumors in a directed fashion. Further, the molecular mechanism for the responses of NSCs to injury has been investigated. Chemokines released during injury, such as SDF-1a, are responsible for the directed migration of human and mouse NSCs to areas of injury in mice. The search for additional mechanisms that operate in the injury environment and how they influence the responses of NSCs during acute and chronic disease is matter of intense research.

In one embodiment, the present invention provides a method for treating a neurodegenerative disease or disorder comprising administering to a subject in need thereof, neural stem cells (NSCs) or pluripotent stem cell (PSC) derived neurons or neuron precursor cells, into the brain of the subject, thereby treating the disorder. In one aspect, the subject is human. In another aspect, the neural stem cells or the PSCs are human. In a further aspect, the PSCs are partially or fully differentiated prior to administration. In an additional embodiment, the PSCs are human embryonic stem cells (hESCs), human parthenogenetic stem cells (hpSCs) or induced pluripotent stem cells (iPSCs). In a preferred aspect, the PSCs are human parthenogenetic stem cells. In one aspect, the neurodegenerative disease or disorder is Alzheimer's Disease, Parkinson's Disease, Amyotrophic Lateral Sclerosis (ALS) or Huntington's Disease. In a specific aspect, the neurodegenerative disease or disorder is Parkinson's disease. In an additional aspect, the NSCs or PSC derived neuron precursor cells differentiate in vivo into dopaminergic neurons. In one aspect, the NSCs or PSC derived neurons or neuron precursor cells increase the levels of dopamine in the subject. In another aspect, the NSCs or PSC derived neurons or neuron precursor cells induce endogenous dopaminergic neurons to release dopamine. In a further aspect, the NSCs are derived by the method comprising obtaining human pluripotent stem cells (hPSCs); and treating the hPSCs with a checkpoint kinase 1 (CK1) inhibitor and a bone morphogenic protein (BMP) inhibitor. In one aspect, the PSC derived neurons or neuron precursor cells are dopaminergic.

As used herein, "neurodegenerative disease or disorder" refers to any disease or disorder which is characterized by progressive loss of neurons or function of neurons. Examples of neurodegenerative diseases or disorder include Alzheimer's Disease, Parkinson's Disease, Amyotrophic Lateral Sclerosis (ALS or Lou Gehrig's Disease) and Huntington's Disease.

Alzheimer's disease is characterized by loss of neurons and synapses in the cerebral cortex and certain subcortical regions. This loss results in gross atrophy of the affected regions, including degeneration in the temporal lobe and parietal lobe, and parts of the frontal cortex and cingulate gyms.

Alzheimer's disease has been hypothesized to be a protein misfolding disease (proteopathy), caused by accumulation of abnormally folded A-beta and tau proteins in the brain. Plaques are made up of small peptides, 39-43 amino acids in length, called beta-amyloid (also written as A-beta or Aβ). Beta-amyloid is a fragment from a larger protein called amyloid precursor protein (APP), a transmembrane protein that penetrates through the neuron's membrane. APP is critical to neuron growth, survival and post-injury repair. In Alzheimer's disease, an unknown process causes APP to be divided into smaller fragments by enzymes through proteolysis. One of these fragments gives rise to fibrils of beta-amyloid, which form clumps that deposit outside neurons in dense formations known as senile plaques.

Parkinson's disease (PD) is the second most common neurodegenerative disorder and manifests as bradykinesia, rigidity, resting tremor and posture instability. The crude prevalence rate of PD has been reported to range from 15 per 100,000 to 12,500 per 100,000, and the incidence of PD from 15 per 100,000 to 328 per 100,000, with the disease being less common in Asian countries. Parkinson's disease is a degenerative disorder of the central nervous system. It results from the death of dopamine-generating cells in the substantia nigra, a region of the midbrain; the cause of cell-death is unknown.

Parkinson's disease (PD) is a neurodegenerative disorder caused by a progressive degeneration of midbrain dopamine (DA) neurons in the substantia nigra pars compacta. The degeneration of DA neurons causes a gradual dysfunction of the motor system leading to symptoms such as tremor, rigidity, and bradykinesia, among others. There is currently no cure for PD and although treatments such as deep brain stimulation and levodopa can alleviate some of the symptoms, they tend to lose efficacy over time. However, the localized nature of the loss of DA neurons in the substantia nigra (SN) makes cell replacement therapy an attractive approach to treating PD patients.

The mechanism by which the brain cells in Parkinson's are lost may consist of an abnormal accumulation of the protein alpha-synuclein bound to ubiquitin in the damaged cells. The alpha-synuclein-ubiquitin complex cannot be directed to the proteosome. This protein accumulation forms proteinaceous cytoplasmic inclusions called Lewy bodies. The latest research on pathogenesis of disease has shown that the death of dopaminergic neurons by alpha-synuclein is due to a defect in the machinery that transports proteins between two major cellular organelles—the endoplasmic reticulum (ER) and the Golgi apparatus. Certain proteins like Rab1 may reverse this defect caused by alpha-synuclein in animal models.

Recent research suggests that impaired axonal transport of alpha-synuclein leads to its accumulation in the Lewy bodies. Experiments have revealed reduced transport rates of both wild-type and two familial Parkinson's disease-associated mutant alpha-synucleins through axons of cultured neurons. Membrane damage by alpha-synuclein could be another Parkinson's disease mechanism.

Huntington's Disease (HD) causes astrogliosis and loss of medium spiny neurons. Areas of the brain are affected according to their structure and the types of neurons they contain, reducing in size as they cumulatively lose cells. The areas affected are mainly in the striatum, but also the frontal and temporal cortices. The striatum's subthalamic nuclei send control signals to the globus pallidus, which initiates and modulates motion. The weaker signals from subthalamic nuclei thus cause reduced initiation and modulation of movement, resulting in the characteristic movements of the disorder.

Mutant Huntingtin is an aggregate-prone protein. During the cells' natural clearance process, these proteins are retrogradely transported to the cell body for destruction by lysosomes. It is a possibility that these mutant protein aggregates damage the retrograde transport of important cargoes such as BDNF by damaging molecular motors as well as microtubules.

Amyotrophic lateral sclerosis (ALS/Lou Gehrig's Disease) is a disease in which motor neurons are selectively targeted for degeneration. In 1993, missense mutations in the gene encoding the antioxidant enzyme Cu/Zn superoxide dismutase 1 (SOD1) were discovered in subsets of patients with familial ALS. This discovery led researchers to focus on unlocking the mechanisms for SOD1-mediated diseases. However, the pathogenic mechanism underlying SOD1 mutant toxicity has yet to be resolved. More recently, TDP-43 and FUS protein aggregates have been implicated in some cases of the disease, and a mutation in chromosome 9 (C9orf72) is thought to be the most common known cause of sporadic ALS.

The methods of deriving neural stem cells (NSCs), dopaminergic (DA) neurons and neuron precursor cells and the resulting stem cells and neurons that are described herein are generated from human pluripotent stem cells (hPSCs), such as embryonic stem cells. As used herein, "embryonic" refers to a range of developmental stages of an organism beginning with a single zygote and ending with a multicellular structure that no longer comprises pluripotent or totipotent cells other than developed gametic cells. In addition to embryos derived by gamete fusion, the term "embryonic" refers to embryos derived by somatic cell nuclear transfer. Human stem cells can be maintained in culture in a pluripotent state without substantial differentiation using methods that are known in the art. Such methods are described, for example, in U.S. Pat. Nos. 5,453,357, 5,670,372, 5,690,926 5,843,780, 6,200,806 and 6,251,671 the disclosures of which are incorporated herein by reference in their entireties.

As used herein, "multipotent" or "multipotent cell" refers to a cell type that can give rise to a limited number of other particular cell types. Examples of multipotent cells include ectodermal cells, endodermal cells, mesodermal cells and neural stem cells which can give rise to limited number of other cells.

As used herein, a "pluripotent cell" refers to a cell that can be maintained in vitro for prolonged, theoretically indefinite period of time in an undifferentiated state, that can give rise to different differentiated tissue types, i.e., ectoderm, mesoderm, and endoderm. Human pluripotent stem cells (hPSCs) include, but are not limited to, human embryonic stem cells (hESCs), human parthenogenetic stem cells (hpSCs) and induced pluripotent stem cells (iPSCs). Methods of obtaining such hPSCs are well known in the art.

One method of obtaining hPSCs is by parthenogenesis. "Parthenogenesis" ("parthenogenically activated" and "parthenogenetically activated" is used herein interchangeably) refers to the process by which activation of the oocyte occurs in the absence of sperm penetration, and refers to the development of an early stage embryo comprising trophectoderm and inner cell mass that is obtained by activation of an oocyte or embryonic cell, e.g., blastomere, comprising DNA of all female origin. In a related aspect, a "parthenote" refers to the resulting cell obtained by such activation. In another related aspect, "blastocyst: refers to a cleavage stage of a fertilized of activated oocyte comprising a hollow ball of cells made of outer trophoblast cells and an inner cell mass (ICM). In a further related aspect, "blastocyst formation" refers to the process, after oocyte fertilization or activation, where the oocyte is subsequently cultured in media for a time to enable it to develop into a hollow ball of cells made of outer trophoblast cells and ICM (e.g., 5 to 6 days).

Another method of obtaining hPSCs is through nuclear transfer. As used herein, "nuclear transfer" refers to the fusion or transplantation of a donor cell or DNA from a donor cell into a suitable recipient cell, typically an oocyte of the same or different species that is treated before, concomitant or after transplant or fusion to remove or inactivate its endogenous nuclear DNA. The donor cell used for nuclear transfer include embryonic and differentiated cells, e.g., somatic and germ cells. The donor cell may be in a proliferative cell cycle (G1, G2, S or M) or non-proliferating (G0 or quiescent). Preferably, the donor cell or DNA from the donor cell is derived from a proliferating mammalian cell culture, e.g., a fibroblast cell culture. The donor cell optionally may be transgenic, i.e., it may comprise one or more genetic addition, substitution or deletion modifications.

A further method for obtaining hPSCs is through the reprogramming of cells to obtain induced pluripotent stem cells. Takahashi et al. (Cell 131, 861-872 (2007)) have disclosed methods for reprogramming differentiated cells, without the use of any embryo or ES (embryonic stem) cell, and establishing an inducible pluripotent stem cell having similar pluripotency and growing abilities to those of an ES cell. Takahashi et al. describe various different nuclear reprogramming factors for differentiated fibroblasts, which include products of the following four genes: an Oct family gene; a Sox family gene; a Klf family gene; and a Myc family gene.

The pluripotent state of the cells is preferably maintained by culturing cells under appropriate conditions, for example, by culturing on a fibroblast feeder layer or another feeder layer or culture that includes leukemia inhibitory factor (LIF). The pluripotent state of such cultured cells can be confirmed by various methods, e.g., (i) confirming the expression of markers characteristic of pluripotent cells; (ii) production of chimeric animals that contain cells that express the genotype of the pluripotent cells; (iii) injection of cells into animals, e.g., SCID mice, with the production of different differentiated cell types in vivo; and (iv) observation of the differentiation of the cells (e.g., when cultured in the absence of feeder layer or LIF) into embryoid bodies and other differentiated cell types in vitro.

The pluripotent state of the cells used in the present invention can be confirmed by various methods. For example, the cells can be tested for the presence or absence of characteristic ES cell markers. In the case of human ES cells, examples of such markers are identified supra, and include SSEA-4, SSEA-3, TRA-1-60, TRA-1-81 and OCT 4, and are known in the art.

The resultant pluripotent cells and cell lines, preferably human pluripotent cells and cell lines have numerous therapeutic and diagnostic applications. Such pluripotent cells may be used for cell transplantation therapies or gene therapy (if genetically modified) in the treatment of numerous disease conditions.

Human pluripotent stem cells (hPSCs) include, but are not limited to, human embryonic stem cells, human parthenogenetic stem cells, induced pluripotent stem cells and cell lines produced by such cells. hPSCs are maintained in culture in a pluripotent state by routine passage until it is desired that neural stem cells be derived. Examples of human parthenogenetic stem cell lines include LLC2P and LLC12PH.

An "NSC" (also referred to as a "multipotent neural stem cell") exhibits one or more of the following properties: 1) expression of Nestin; 2) expression of Sox2; 3) expression of Musashil; 4) ability to undergo self-renewal, either as a monolayer or in suspension cultures as neurospheres; 5) ability to differentiate into neurons, specific subtypes of neurons, astrocytes, and oligodendrocytes; and 6) morphological characteristics typical for NSCs.

NSCs are self-renewing, multipotent cells that generate the main phenotypes of the nervous system. NSCs primarily differentiate into neurons, astrocytes, and oligodendrocytes.

NSCs can be identified by detecting increased expression of neural stem cell markers, which include, but are not limited to: ABCG2, ASCL1/Mash1, beta-III Tubulin, BMI-1, Brg1, BRN2, CDCP1, CD113, CD15, CXCR4, DCX, FABP, FABP7/B-SLAIN1, FABP8/M-FABP, FGF R4, FOXA2, FOXO4, Frizzled-9, GFAP, Glut1, HOXB1, LMX1A, MAP2, Musashi-1, Musashi-2, Nestin, NeuroD1, Noggin, Notch-1, Notch-2, Nucleostemin, Oligodendrocyte Marker O4, OTX2, PAX6, PDGF R alpha, Prominin 2, SOX1, SOX2, SOX3, SOX9, SOX11, SOX21, SSEA-1, ST6GALNAC5, TUBB3, TRAF-4 and/or Vimentin.

As used herein, "neural stem cell inducing compound" is a compound that induces a hPSCs to become a NSC. Such compounds include, but are not limited to, checkpoint kinase 1 (CK1) inhibitors and bone morphogenic protein (BPM) inhibitors. Examples of CK1 inhibitors include, but are not limited to, SB-218078, Hymenialdisine, Debromohymenialdisine, PD0166285, 13-Hydroxy-15-oxozoapat line, granulatimide, isogranulatimide, and 527888. Examples of BMP inhibitors include, but are not limited to, Dorsomorphin, LD-193189 and DMH-1.

Once NSCs are derived, the cells may be maintained in vitro for prolonged, theoretically indefinite periods of time retaining the ability to differentiate into other neural cell types, such as astrocytes, neurons and oligodendrocytes. As described in the Examples, hPSCs derived NSCs can be grown on Matrigel coated plates in NSC medium for at least seven passages.

PSCs, NSCs and PSC derived neuron precursor cells can be differentiated into dopaminergic neurons under defined chemical conditions.

As used herein, "differentiation" refers to a change that occurs in cells to cause those cells to assume certain specialized functions and to lose the ability to change into certain other specialized functional units. Cells capable of differentiation may be any of totipotent, pluripotent or multipotent cells. Differentiation may be partial or complete with respect to mature adult cells.

"Differentiated cell" refers to a non-embryonic cell that possesses a particular differentiated, i.e., non-embryonic, state. The three earliest differentiated cell types are endoderm, mesoderm, and ectoderm.

NSCs derived from PSCs are multipotent and can be differentiated into several neural cell types including neurons, astrocytes and oligodendrocytes.

A neuron is an electrically excitable cell that processes and transmits information through electrical and chemical signals. A chemical signal occurs via a synapse, a specialized connection with other cells. Neurons connect to each other to form neural networks. Neurons are the core components of the nervous system, which includes the brain, spinal cord, and peripheral ganglia. A number of specialized types of neurons exist: sensory neurons respond to touch, sound, light and numerous other stimuli affecting cells of the sensory organs that then send signals to the spinal cord and brain. Motor neurons receive signals from the brain and spinal cord, cause muscle contractions, and affect glands. Interneurons connect neurons to other neurons within the same region of the brain or spinal cord. There are several types of neurons: cholinergic, GABAergic, Glutamatergic, Dopaminergic and Serotonergic.

Cholinergic neurons. Acetylcholine is released from pre-synaptic neurons into the synaptic cleft. It acts as a ligand for both ligand-gated ion channels and metabotropic (GPCRs) muscarinic receptors. Nicotinic receptors, are pentameric ligand-gated ion channels composed of alpha and beta subunits that bind nicotine. Ligand binding opens the channel causing influx of $Na^+$ depolarization and increases the probability of presynaptic neurotransmitter release.

GABAergic neurons—gamma aminobutyric acid. GABA is one of two neuroinhibitors in the CNS, the other being Glycine. GABA has a homologous function to ACh, gating anion channels that allow $Cl^-$ ions to enter the post synaptic neuron. $Cl^-$ causes hyperpolarization within the neuron, decreasing the probability of an action potential firing as the voltage becomes more negative (recall that for an action potential to fire, a positive voltage threshold must be reached).

Glutamatergic neurons. Glutamate is one of two primary excitatory amino acids, the other being Aspartate. Glutamate receptors are one of four categories, three of which are ligand-gated ion channels and one of which is a G-protein coupled receptor (often referred to as GPCR). AMPA and Kainate receptors both function as cation channels permeable to Na+ cation channels mediating fast excitatory synaptic transmission. NMDA receptors are another cation channel that is more permeable to $Ca^{2+}$. The function of NMDA receptors is dependent on Glycine receptor binding as a co-agonist within the channel pore. NMDA receptors do not function without both ligands present. Metabotropic receptors, GPCRs modulate synaptic transmission and post-synaptic excitability. Glutamate can cause excitotoxicity when blood flow to the brain is interrupted, resulting in brain damage. When blood flow is suppressed, glutamate is released from presynaptic neurons causing NMDA and AMPA receptor activation more so than would normally be the case outside of stress conditions, leading to elevated $Ca^{2+}$ and $Na^+$ entering the post synaptic neuron and cell damage.

Dopaminergic neurons. Dopamine is a neurotransmitter that acts on D1 type (D1 and D5) Gs coupled receptors, which increase cAMP and PKA, and D2 type (D2, D3, and D4) receptors, which activate Gi-coupled receptors that decrease cAMP and PKA. Dopamine is connected to mood and behavior, and modulates both pre and post synaptic neurotransmission. Loss of dopamine neurons in the substantia nigra has been linked to Parkinson's disease.

Serotonergic neurons. Serotonin, (5-Hydroxytryptamine, 5-HT), can act as excitatory or inhibitory. Of the four 5-HT receptor classes, three are GPCR and one is ligand gated cation channel. Serotonin is synthesized from tryptophan by tryptophan hydroxylase, and then further by aromatic acid decarboxylase. A lack of 5-HT at postsynaptic neurons has been linked to depression. Drugs that block the presynaptic serotonin transporter are used for treatment, such as Prozac and Zoloft.

Neurons may be identified by expression of neuronal markers Tuj1 (beta-III-tubulin); MAP-2 (microtubule associated protein 2, other MAP genes such as MAP-1 or -5 may also be used); anti-axonal growth clones; ChAT (choline acetyltransferase); CgA (anti-chromagranin A); DARRP (dopamine and cAMP-regulated phosphoprotein); DAT (dopamine transporter); GAD (glutamic acid decarboxylase); GAP (growth associated protein); anti-HuC protein; anti-HuD protein; .alpha.-internexin; NeuN (neuron-specific nuclear protein); NF (neurofilament); NGF (nerve growth factor); .gamma.-SE (neuron specific enolase); peripherin; PH8; PGP (protein gene product); SERT (serotonin transporter); synapsin; Tau (neurofibrillary tangle protein); anti-Thy-1; TRK (tyrosine kinase receptor); TRH (tryptophan hydroxylase); anti-TUC protein; TH (tyrosine hydroxylase); VRL (vanilloid receptor like protein); VGAT (vesicular GABA transporter), VGLUT (vesicular glutamate transporter).

A neuron generated by inducing differentiation of a NSC or a PSC derived neuron precursor cell can be tested according to functional criteria. For example, calcium flux can be measured by any standard technique, in response to a neurotransmitter, or other environmental condition known to affect neurons in vivo. First, neuron-like cells in the population are identified by morphological criteria, or by a marker such as NCAM. The neurotransmitter or condition is then applied to the cell, and the response is monitored. The cells can also be subjected to standard patch-clamp techniques, to determine whether there is evidence for an action potential, and what the lag time is between applied potential and response. Differentiation of a NSC or a PSC derived neuron precursor cells can generate cultures that contain subpopulations that have morphological characteristics of neurons, are NCAM or MAP-2 positive, and show a response to one or more of GABA, acetylcholine, ATP, and high sodium concentration, glutamate, glycine, ascorbic acid, dopamine, or norepinephrine. In some embodiments, a subject differentiated NCAM or MAP-2 positive can also exhibit an action potential in a patch-clamp system.

Markers for dopaminergic neurons include, but are not limited to, TUJ1, TH, Dat, Foxa2, Nurr-1, Girk2, MAPT, SYT4, FOXA1, DDC, ASCL1, PINK1, PAX5, LMX1B, PITX3, NURR-1, LMX1A, EN1, PAX2, TFF3, PITX2, DCX, MAP2, PITX1 or VMAT2, or any combination thereof.

PSCs, NSCs and PSC derived neuron precursor cells can be differentiated into neurons, including dopaminergic (DA) neurons. One method to differentiate PSCs, NSCs and PSC derived neuron precursor cells into DA neurons is to treat the cells with a dopaminergic neuron inducing compound. Such compounds include Homoquinolinic acid, L-Cysteine-sulfinic acid, Kynurenic acid, (R)-(+)-HA-966, m-Chlorophenylbiguanide hydrochloride, Calpeptin, Dimaprit dihydrochloride, 8-Hydroxy-DPAT hydrobromide, trans-4-Hydroxycrotonic acid, Fasudil hydrochloride, Thioperamide, Retinoic acid, AM580, TTNPB, Remoxipride hydrochloride, ICI 215,001 hydrochloride, Imiloxan hydrochloride, Spiperone hydrochloride, Kenpaullone, CL 218872, CV 1808, Ro 15-4513, Linopirdine dihydrochloride, Guggulsterone, Ch 55, 3-MATIDA, SEW 2871, Immethridine dihydrobromide, LY 364947, Tranylcypromine hydrochloride, (−)-Cytisine or Nilutamide, or any combination thereof.

The resulting DA neuron will be characterized by expression of dopaminergic neuron cell markers including TUJ1, TH, Dat, Foxa2, Nurr-1, Girk2, MAPT, SYT4, FOXA1, DDC, ASCL1, PINK1, PAX5, LMX1B, PITX3, NURR-1, LMX1A, EN1, PAX2, TFF3, PITX2, DCX, MAP2, PITX1 or VMAT2, or any combination thereof.

The NSCs and PSC derived neurons and neuron precursor cells may be administered the subject by any route known in the art. Examples include, oral, intravenous, subcutaneous and intramuscular administration. The NSCs and PSC derived neurons and neuron precursor cells may also be directly injected into the brain of the subject, either directly at the affected area of the brain or adjacent to the affected area.

As described in the Examples, the disclosed methods increased dopamine levels as well as resulted in behavioral improvements in PD models. It was also observed that NSCs migrate from the site of injection. Further, there was a prevention or slowing of progression of PD symptoms. There was also an improvement in the presynaptic activity as well as an increase in the number and innervation of the TH+ neurons. Additionally both stimulation of endogenous DA neuron activity and spontaneous in vitro differentiation if NSCs and PSC derived neuron precursor cells was observed.

In an additional embodiment, the present invention provides a method of increasing dopamine levels in a subject comprising administering to a subject in need thereof, NSCs or pluripotent stem cell (PSC) derived neurons and neuron precursor cells, into the brain of the subject, thereby increasing dopamine levels.

In another embodiment, the present invention provides a method of inducing endogenous dopaminergic (DA) neurons to release dopamine comprising administering to a subject in need thereof, neural stem cells (NSCs) or pluripotent stem cell (PSC) derived neurons or neuron precursor cells, into the brain of the subject, thereby inducing the endogenous DA neurons to release dopamine.

In a further embodiment, the present invention provides a method of treating a subject with a neurodegenerative disease or disorder comprising: obtaining human pluripotent stem cells (hPSCs); treating the hPSCs with a checkpoint kinase 1 (CK1) inhibitor and a bone morphogenic protein (BMP) inhibitor; and administering the cells into the brain of the subject, thereby treating the neurodegenerative disorder. In one aspect, hPSCs are human embryonic stem cells (hESCs), human parthenogenetic stem cells (hpSCs) or induced pluripotent stem cells (iPSCs). In a preferred aspect, the hPSCs are obtained by parthenogenesis or nuclear transfer. In an additional aspect, the hPSCs are obtained by the method comprising: parthenogenetically activating a human oocyte, wherein activating comprises: contacting the oocyte with an ionophore at high $O_2$ tension and contacting the oocyte with a serine-threonine kinase inhibitor under low $O_2$ tension; cultivating the activated oocyte at low $O_2$ tension until blastocyst formation; transferring the blastocyst to a layer of feeder cells, and culturing the transferred blastocyst under high $O_2$ tension; mechanically isolating an inner cell mass (ICM) from trophectoderm of the blastocyst and culturing the cells of the ICM on a layer of feeder cells under high $O_2$ tension, thereby producing human stem cells. In one aspect, the CK1 inhibitor is SB2180708. In another aspect, the BMP inhibitor is Dorsomorphin, LD-193189 or DMH-1.

In one embodiment, the present invention provides a method of treating a subject with a neurodegenerative disease or disorder comprising: obtaining human pluripotent stem cells (hPSCs); treating the cells with a checkpoint kinase 1 (CK1) inhibitor and a bone morphogenic protein (BMP) inhibitor; treating the cells with guggulsterone; and administering the cells into the brain of the subject, thereby treating the neurodegenerative disorder.

The following examples are intended to illustrate, but not limit the invention.

Example 1 hPSC-NSCS

To derive NSCs, primitive neuroepithelium was induced by switching the hPSCs grown on Matrigel from StemPro to N2B27 medium supplemented with 5 µM SB218078 and 1 µM DMH-1. After 6 days in the presence of these neural inducers, Pax6, an early marker of neural induction, was significantly up-regulated. On day 7, the neuralized hPSCs were switched to NSC medium and then dissociated to derive proliferative NSCs. After 4 passages, the hPSC derived NSC (hPSC-NSC) population was 98% positive for Nestin, 96% for Musashi-1, 95% for PAX6, 0% for OCT4 and gene expression microarray analysis revealed up-regulation of putative NSC markers including FABP7, BRN2, SOX3, ST6GALNAC5, CXCR4, DCX, NES, and MSI.

Specifically, the hPSC lines [human embryonic stem cell line WA-09 and human parthenogenetic stem cell lines LLC2P and LLC12PH (International Stem Cell Corporation)] were first maintained on a mitomycin-C inactivated mouse embryonic fibroblast (Millipore) feeder layer in embryonic stem cell medium: Knock Out DMEM/F12 (Life Technologies), 2 mM L-glutamine (GlutaMax-I, Invitrogen), 0.1 mM MEM nonessential amino acids (Life Technology), 0.1 mM β-mercaptoethanol (Life Technologies), penicillin/streptomycin/amphotericin B (100 U/100 µg/250 ng) (MP Biomedicals) and 5 ng/ml bFGF (Peprotech). Cells were passaged with dispase (Life Technologies) every 5-7 days with split ratio of 1:4 or 1:6. The hPSCs were then transferred to Matrigel (BD Biosciences) coated plates and grown with Stem Pro hESC SFM medium (Invitrogen): DMEM/F12 with GlutaMAX, 1× STEMPRO hESC SFM Growth Supplement, 1.8% Bovine Serum Albumin, 8 ng/mL bFGF and 0.1 mM 2-Mercaptoethanol.

Example 2 hPSC Derived Dopaminergic Neurons hPSC-NSC were first primed into DA neuron precursor cells with 100 ng/mL FGF8 and 2 µM Purmorphamine for 7 days. The DA neuron precursor cells were plated at 2000 cells/well of a 96-well plate and treated with guggulsterone (GS) at 2.5 µM for two weeks. After 30 days of differentiation, GS-treated neurons appeared mature with elaborate neurite extensions. At this stage, the derived cells expressed not only the major neuronal marker β-III-tubulin (TUJ1), but also the important DA neuron markers tyrosine hydroxylase (TH), the dopamine transporter (Dat), Foxa2, Nurr-1, and Girk2. Furthermore, FACS analysis revealed that more than 97% of the cells gated were TH positive.

Figure 2A:
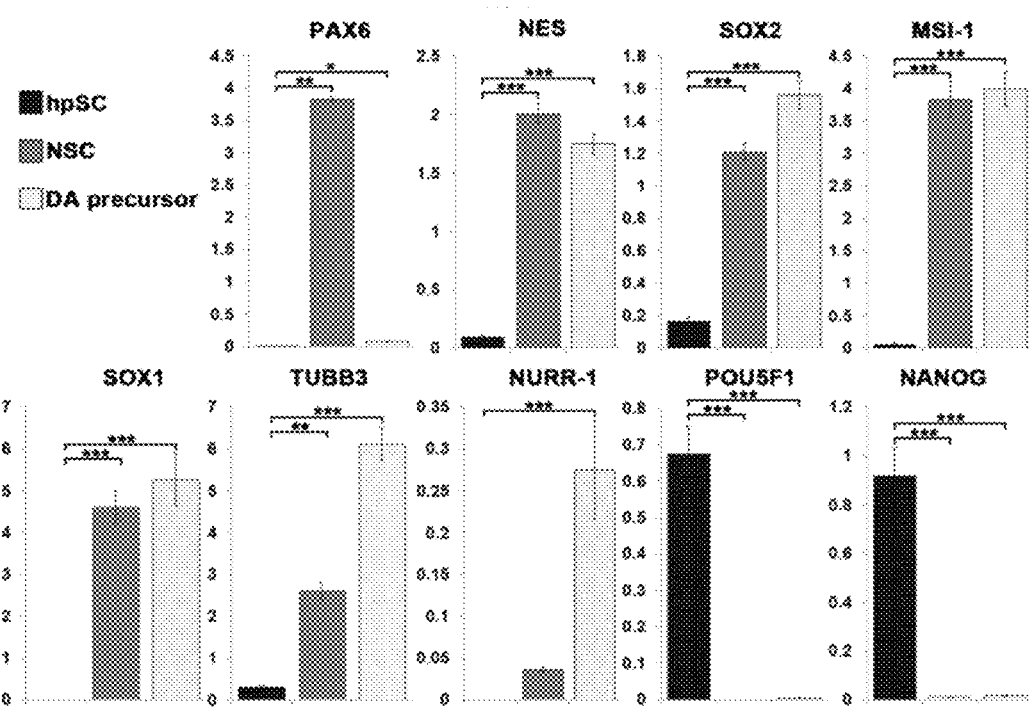
FIGS. 2A-2B show gene expression analysis of hPSC derived NSCs and DA neuron precursor cells.

The method specifically involved treating both hESC-H9-NSCs (Invitrogen) and hPSC-NSCs with Purmorphamine (2 µM) and FGF8 (100 ng/mL) in NB medium [NeuroBasal medium, 1× GlutaMAX, 1× N2/B27 Supplement (Invitrogen)] for 7 days. After 7 days of Purmorphamine and FGF8 treatment, the NSCs were dissociated with Accutase (Sigma) and plated 20,000 cells/mL into Matrigel coated 96 well plates and treated with guggulsterone at 2.5 µM final concentration for two weeks. Two weeks after treatment with small molecules, all wells were visually observed and scored based on neurite density and dopamine release. For measuring neurite density, cells were fixed with 4% paraformaldehyde and phase contrast images were acquired using Cellavista Cell Imaging System (Roche Applied Science) from randomly selected fields. Neurite density was measured using the Cellavista density software image processing program. Each experimental condition was done in duplicate wells, and at least three independent experiments were conducted to acquire the final results. Gene expression analysis of hPSC derived NSCs, DA neuron precursor cells and hPSC determined that there were 801 up regulated genes in the DA neuron precursor cells and 566 up regulated genes in the NSCs (FIG. 2).

Example 3

Implantation of hPSC-Derived NSCS into 6-OHDA-Induced Parkinson's Disease Rat Model Adult female Sprague-Dawley rats with unilateral, medial forebrain bundle 6-OHDA lesions of the nigro-striatal pathway were purchased from Charles River. This Parkinson's disease rat model is based on a 6-OHDA induced lesion on the left brain hemisphere. A rotational challenge test was administered by Charles River 5-7 days post-surgery to verify surgical success with a subcutaneous injection of 0.2 mg/kg of apomorphine hydrochloride. The drug was administered and the rotational count began upon the first rotation. The count continued for 5 minutes and the final count was divided by 5 for the rotations per minute. A successful surgery was determined by a minimum of 5 rotations per minute. All information was logged on the Parkinson Test Sheet: Animal Number, body weight, injection time, start time, end time, total rotations, rotations per minute, and Pass or Fail.

Three weeks after 6-OHDA lesion, rats were anesthetized and placed in a stereotactic frame. A burr hole was drilled over the target area and 5×105 hPSC-NSCs were injected into the striatum of each rat, divided into two sites. 5 µl of the cell suspension was injected per site (100,000 cells/W) at a rate of 0.5 µl/min over a period of 15 min. Control rats received PBS.

Animals were injected with amphetamine before transplantation and 12 weeks post-transplantation to test rotational behavior. At the end of the study, animals were sacrificed, blood collected for ELISA analysis of dopamine concentration and a complete necropsy was performed. For immunocytochemistry, whole brains were collected after transcardial perfusion with PBS. For PCR, samples were collected and placed in PCR buffer.

Figure 2B:
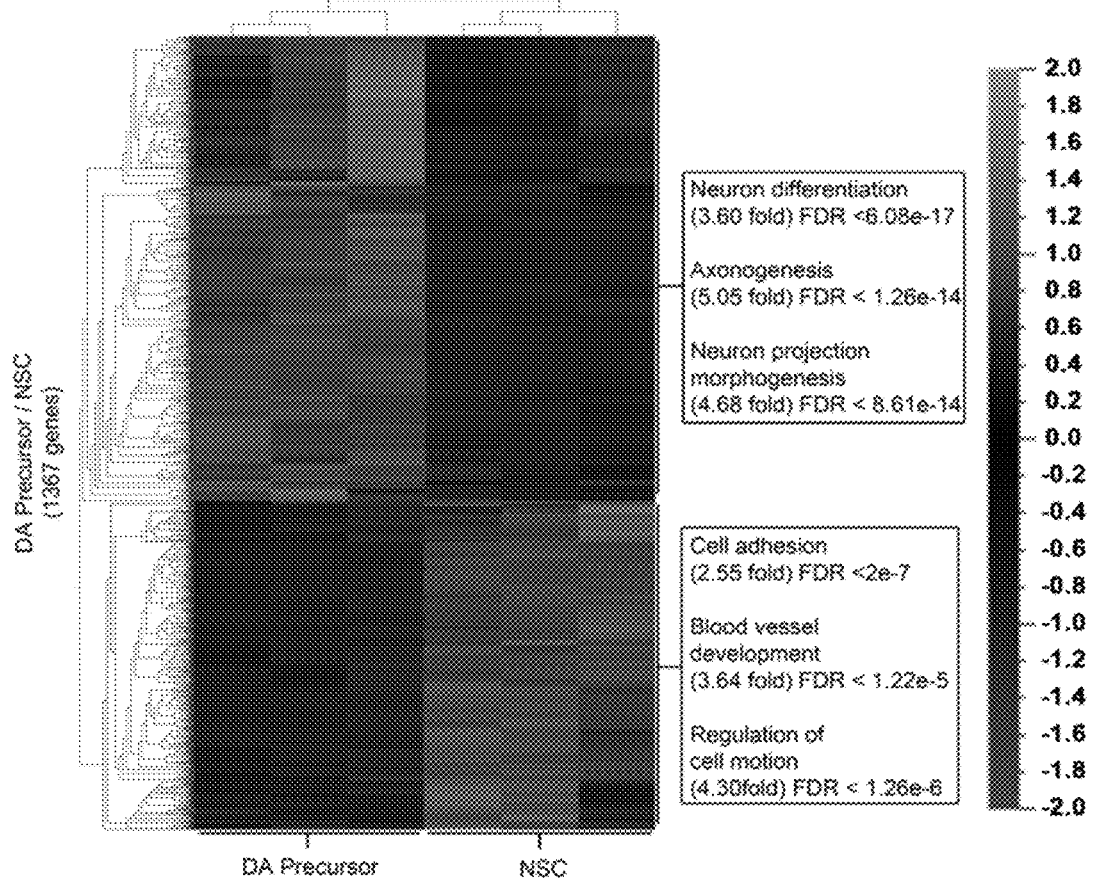

Following cell transplantation of NSCs and DA neuron precursor cells into 6-OHDA-lesioned rats the animals remained healthy with no abnormal behaviors other than parkinsonism for the entire 28-week study period. A significant behavioral improvement was observed for both cell types, as evidenced by the amphetamine-induced rotational test (FIG. 3A). Higher dopamine levels were observed in homogenized rodent whole brain tissue grafted with NSCs than in brain tissue grafted with DA neuron precursor cells or in sham control brain tissue (FIG. 3B). Both NSCs and DA neuron precursor cells demonstrated long-term survival and successful engraftment 28-weeks post-transplantation (FIG. 3C and FIG. 3D). In the rodents that were injected with DA neuron precursor cells, the implanted cells formed a compact graft at the site of injection, whereas in the rodents implanted with NSCs the cells were dispersed around the injection site (FIG. 3C) to a greater extent. Three times the number of NSCs were detected in the brains compared with DA neuron precursor cells, which corresponds to approximately 60% survival for NSCs and 20% for DA neuron precursor cells (FIG. 3D). The higher survival of NSCs can be explained by the RNA-Sequencing data which showed the enrichment in NSCs of genes associated with cell adhesion, blood vessel development, and regulation of cell motion, all of which promote successful engraftment (FIG. 2B). Another possible reason could be that NSCs proliferated in vivo, but NSCs did not co-stain with proliferation marker Ki67 (FIG. 3E).

Figure 4A:
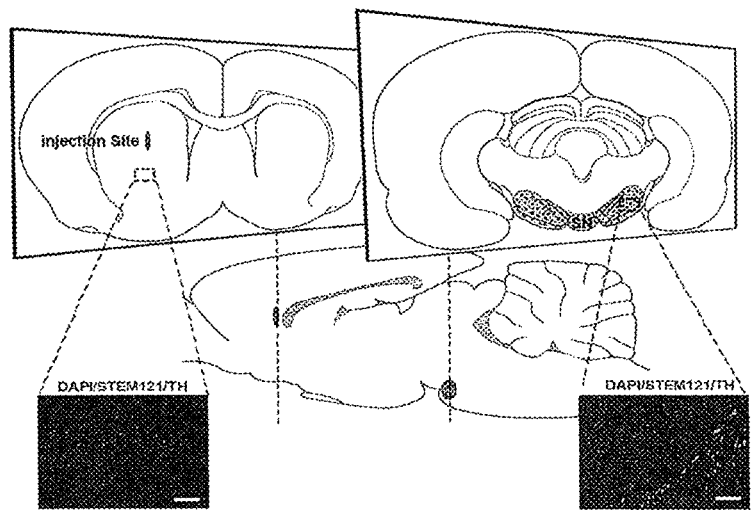
FIGS. 4A-4C show migration and immune response of grafts in 6-OHDA lesioned rats.
Figure 4B:
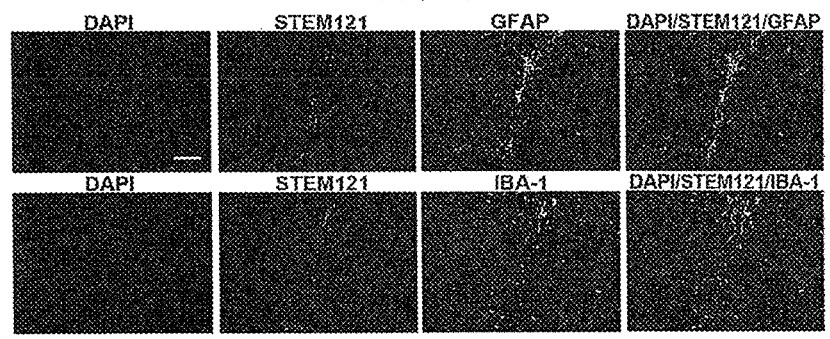
Figure 4C:
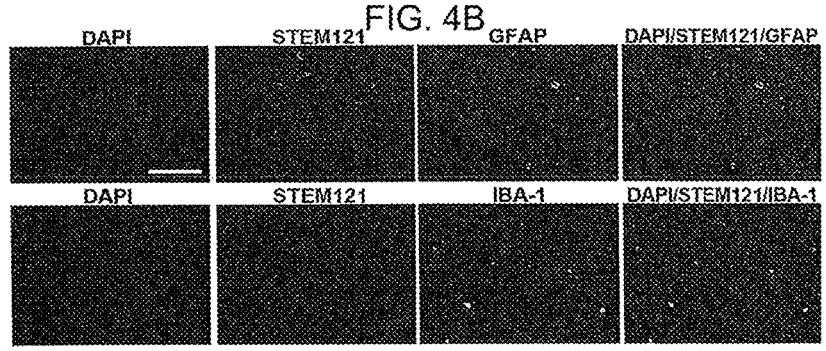

Significant migration of NSCs was observed from the site of injection in the striatum to the substantia nigra, possibly along the nigrostriatal pathway (FIG. 4A). Implanted NSCs were found close to the injection site, but more predominantly in the substantia nigra where the host DA neurons are present. Engrafted NSCs migrated 8-10 mm from the site of injection and were even found in the substantia nigra contralateral to the injection side (FIG. 4A). Not only was there no migration of the DA neuron precursor cell grafts from the site of injection, but the cells also appeared to elicit a possible immune response as evidenced by the increase in IBA-1 positive host microglia and astrocyte numbers (GFAP+) in the relevant graft area (FIG. 4B) in spite of immunosuppression. In contrast, engrafted NSCs were not surrounded by host glial cells or abundant microglia, indicating a significantly less pronounced immunogenic response (FIG. 4C). Gross necropsy results revealed the absence of abnormal tissue or tumors and biodistribution analysis demonstrated that there were no human cells present in any of the other organs analyzed.

Example 4

Implantation of hPSC-Derived NSCS in Non-Human Primate Brain with MPTP-Induced Parkinson's Disease The non-human primates used in this study were African green monkeys (*Chlorocebus sabaeus*) from St. Kitts, West Indies. The St. Kitts/African green monkey was chosen because it is the most complete and identical model of human Parkinson's disease that has been studied of any species. Surgeries were performed under an approved Animal Care and Use Committee (ACUC) protocol in St. Kitts Biomedical Research Foundation at St. Kitts, West Indies. Asymptomatic monkeys were generated by injecting cumulative doses over a 5-day period of 1.5 mg/kg MPTP to induce degeneration of the nigrostriatal pathway, in which dopamine depletion is produced but without functional impairments. All monkeys in this study were immunosuppressed 1 day prior to grafting and continued receiving the drugs until sacrifice. The cellular suspension of hPSC-NSCs was drawn into a 22 g cannula immediately prior to implantation into the target sites. The sample was implanted into the brain using standard stereotactic procedures and verified stereotaxic coordinates. Insertion was performed slowly over a 2 minute period and the tip of the cannula was permitted to remain in the implantation site for at least 2 minutes prior to injection. Cells were extruded using a controlled perfusion pump (Stoelting) at a maximum rate of 1 µl/min, with a 2 minute delay before cannula withdrawal at a rate of 1 µm/minute. The stereotaxic targets were one side only: 21 mm AP, 3.5 mm Lateral, and Vertical 18.6 mm from earbar zero for the caudate, and the same AP and Vertical for the putamen, but Lateral 10 mm. The substantia nigra target was AP 11.1, Lateral 3.5, and Vertical 12.1.

The engraftment of hPSC-NSCs was conducted under sterile conditions. Two host monkeys were used for the study and were operated simultaneously for both control and efficiency reasons. A special Kopf drill was used to drill small, 2 mm holes, at the site of each entry point, using a diamond covered spherical drill. The carrier was then changed to one carrying a Hamilton syringe with a 22 gauge needle. Using sterile technique, hPSC-NSCs were drawn up into a sterile 22-gauge needle. Control monkeys received vehicle control PBS instead. Needles were mounted on 100 µl Hamilton syringes in Stoelting microinfusion pumps and lowered into appropriate sites in the host brain according to standard stereotaxic procedures. The cells were injected under the control of a Stoelting syringe pump, at a rate of 1 µl/minute. After a 2 minute wait, the needles were then withdrawn at a rate of 1 mm/minute for 5 mm and then "slowly" until out of the brain. After all injections were complete, the head was irrigated and the muscle, subcutaneous layer, and skin were closed using standard surgical methods (muscle, subcutaneous, and skin layer closures with chromic and vicryl suture, followed by Dermabond to seal wound edges). The animal was then removed from the stereotaxic device and monitored continuously until awake. Subjects received post-operative analgesics (for 48 hours) and were monitored until vital signs were stable and the animals were awake. They recovered well from the surgery without complications.

Parkinson scores were recorded by blinded observers who scored the monkeys twice per day, 5 days per week by using a published and validated quantitative time-sampling method, which has been shown empirically to sample Parkinsonian behaviors efficiently and accurately. At the time of surgery Parkinson's scores were below 10, which mean that the monkeys were asymptomatic and did not have functional impairments or clinical symptoms of PD.

To evaluate the effects of the cells in a more relevant Parkinson's disease model, cells were transplanted into MPTP-exposed monkeys. These monkeys are known from prior studies to have significant dopamine depletion, but to be generally asymptomatic and able to care for themselves. This model is useful for evaluating cell survival and differentiation effects in a dopamine-depleted environment. Transplanted primates maintained stable ratings and scores of Parkinsonism and summary healthy behavior scores throughout the 14-week study period (FIG. 5A-5D). These data confirm that these monkeys showed stable very low scores of Parkinsonism as well as high levels of healthy behavior throughout the follow up period. Importantly, no adverse events such as dyskinesia or dystonia, deformations, tumors, or overgrowth were observed, indicating that the transplanted cells were safe and well tolerated by the experimental animals. Most importantly, the presence of undifferentiated, pluripotent, OCT-4 positive cells was not detected in any of the grafts.

Figure 6A:
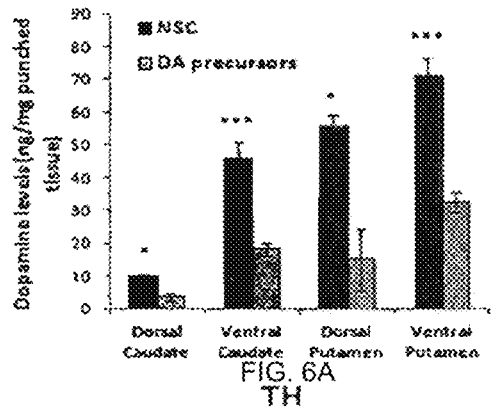
FIGS. 6A-6D show biochemical and histological analysis of transplanted MPTP treated non-human primates.
Figure 6B:
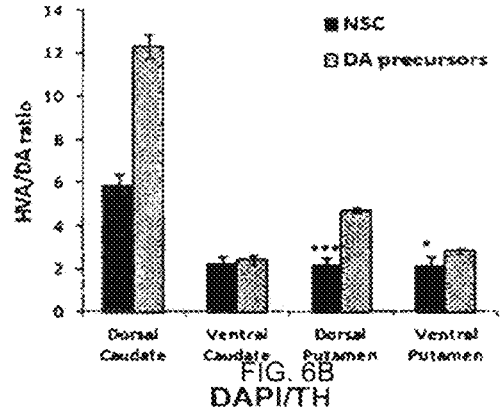
Figure 6C:
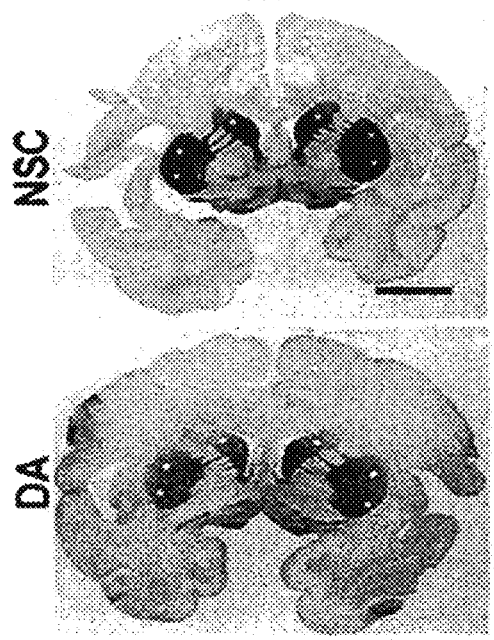
Figure 6D:
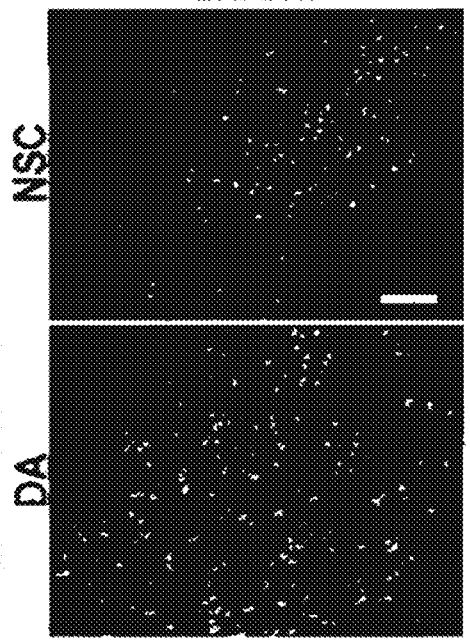

To measure the dopamine levels, tissue punches were taken at eight different sites in the striatum close to some of the injection sites. Primates transplanted with NSCs demonstrated higher post-implantation dopamine levels than animals transplanted DA neuron precursor cells (FIG. 6A). Dopamine turnover, as reflected by the homovanillic acid/dopamine (HVA/DA) ratio, was also normalized in the primates transplanted with NSCs indicating an improvement in the pre-synaptic activity in the existing dopaminergic neurons (FIG. 6B). Additionally, higher number and innervation of TH+ neurons was observed in the striatum (FIG. 6C) and substantia nigra (FIG. 6D) of primates transplanted with NSCs as compared to DA neuron precursor cells. Additionally, surviving DA neuron precursor cells formed compact grafts surrounded by host glial cells (GFAP) and host microglia (IBA-1) (FIG. 7A), whereas NSCs were dispersed and did not have glial scarring or host microglia surrounding the graft (FIG. 7A), as was observed in rodents (FIG. 4A-4C). These analyses indicate that despite the survival of the DA neuron precursor cell grafts, the functional ability of DA neuron precursor cells to increase DA levels may be compromised by the host immune response.

Further characterization of the DA neuron precursor cell grafts in monkeys confirmed their neuronal identity (TUJ1+) and revealed that some of the DA neuron precursor cells further matured in vivo into DA neurons (TH+, NURR1+, and FOXA2+) (FIG. 7B). In contrast, a significant proportion of the transplanted NSCs remained in an undifferentiated state (Nestin+) (FIG. 7C). NSCs retained migratory activity and preferentially migrated along the nigrostriatal pathway (FIG. 7C) and appeared to be in close contact with the host DA neurons in the substantia nigra possible promoting host neural repair (FIG. 7D). Supporting this view, it was found that NSCs secrete higher levels of GDNF and BDNF in vitro and in vivo than DA neuron precursor cells, possibly explaining the greater regeneration observed in the nigrostriatal system in the NSC transplanted animals. A small percentage of NSCs were observed to spontaneously differentiate into TH+ cells, as shown by co-staining of the cells with dopaminergic markers G-protein-regulated inward-rectifier potassium channel 2 (GIRK2), vesicular monoamine transporter 2 (VMAT2) (FIG. 7E). NSCs differentiated into neurons that express synaptophysin (SYP), an integral membrane protein of presynaptic vesicles, supporting their functional engraftment (FIG. 7E). The combined effects of cell replacement, immunomodulation, and neuroprotective cross-talk of NSCs with the host DA neurons may be responsible for the higher number of TH+ neurons observed in the substantia nigra and overall higher DA levels in the striatum (FIG. 6A-6D).

Although the invention has been described with reference to the above example, it will be understood that modifications and variations are encompassed within the spirit and scope of the invention. Accordingly, the invention is limited only by the following claims.

What is claimed is:

1. A method of producing pluripotent stem cell (PSC) derived neural stem cells (NSCs), neuron precursor cells or neurons comprising:
   a) producing human parthenogenetic stem cell (hpSC) by the method comprising:
      i) parthenogenetically activating a human oocyte by contacting the oocyte with an ionophore at high $O_2$ tension and contacting the oocyte with a serine-threonine kinase inhibitor under low $O_2$ tension;
      ii) cultivating the activated oocyte of (i) at low $O_2$ tension until blastocyst formation;
      iii) transferring the blastocyst to a layer of feeder cells, and culturing the transferred blastocyst under high $O_2$ tension;
      iv) mechanically isolating an inner cell mass (ICM) from trophectoderm of the blastocyst of (iii); and
      v) culturing the cells of the ICM of (iv) on a layer of feeder cells, wherein culturing (v) is carried out under high $O_2$ tension, thereby producing hpSCs; and
   b) treating the hpSCs with SB2180708 and a bone morphogenic (BMP) inhibitor,
thereby producing neural stem cells (NSCs), neuron precursor cells or neurons.

2. The method of claim 1, wherein the BMP inhibitor is selected from the group consisting of Dorsomorphin, LD-193189 and DMH-1.

3. The method of claim 2, wherein the BMP inhibitor is DMH-1.

4. The method of claim 1, further comprising identifying the expression of at least one molecular marker on NSCs selected from the group consisting of Nestin, SRY (sex determining region Y)-box 2 (SOX2), Paired box protein Pax-6 (PAX6), Fatty acid binding protein (FABP7), POU domain class 3 transcription factor 2 (BRN2), SRY (Sex Determining Region Y)-Box 3 (SOX3), ST6 N-Acetylgalactosamine Alpha-2,6-Sialyltransferase 5 (ST6GALNAC5), C-X-C Motif Chemokine Receptor 4 (CXCR4), Doublecortin (DCX), and/or Musashi-1 (MSI1).

5. The method of claim 1, further comprising identifying increased expression of neural stem cell markers compared to the hpSCs.

6. The method of claim 5, wherein the neural stem cell markers are selected from the group consisting of ATP Binding Cassette Subfamily G Member 2 (ABCG2), Achaete-scute homolog 1 (ASCL1/Mash1), anti-axonal growth clones, beta-III Tubulin, Polycomb complex protein BMI-1 (BMI-1), Brahma-related gene-1 (Brg1), BRN2, choline acetyltransferase (ChAT), chromagranin A (CgA), CUB Domain Containing Protein 1 (CDCP1), Nectin-3 (CD113), CD15, CXCR4, DCX, dopamine and cAMP-regulated phosphoprotein (DARRP), dopamine transporter (DAT), fatty-acid-binding protein (FABP), Fatty acid-binding protein 7 (FABP7), SLAIN Motif Family Member 1 (SLAIN1), myelin-fatty acid-binding protein (FABP8/M-FABP), Fibroblast growth factor receptor 4 (FGF R4), Forkhead Box A2 (FOXA2), Forkhead Box 04 (FOXO4), Frizzled-9, Glial fibrillary acidic protein (GFAP), Glucose transporter 1 (Glut1), glutamic acid decarboxylase (GAD), growth associated protein (GAP), homeobox B1 (HOXB1), HuC protein, HuD protein, LIM Homeobox Transcription Factor 1 Alpha (LMX1A), Microtubule Associated Protein 1 (MAP1), Microtubule Associated Protein 2 (MAP2), microtubule-associated protein 5 (MAPS), Musashi-1, Musashi-2, Nestin, Neurogenic differentiation 1 (NeuroD1), alpha-internexin, neuron-specific nuclear protein (NeuN), neurofilament (NF), nerve growth factor (NGF), neuron specific enolase (NSE), Noggin, Notch-1, Notch-2, Nucleostemin, Oligodendrocyte Marker O4, Orthodenticle Homeobox 2 (OTX2), PAX6, peripherin, PH8, platelet-derived growth factor receptor A (PDGF R alpha), Prominin 2, protein gene product (PGP), serotonin transporter (SERT), SRY-box transcription factor 1 (SOX1), SRY-box transcription factor 2 (SOX2), SRY-box transcription factor 3 (SOX3), SRY-box transcription factor 9 (SOX9), SRY-box transcription factor 11 (SOX11), SRY-box transcription factor 21 (SOX21), Stage specific embryonic antigen-1 (SSEA-1), ST6GALNAC5, synapsin; neurofibrillary tangle protein (Tau), Thy-1, TNF receptor-associated factor 4 (TRAF-4), tyrosine kinase receptor (TRK), tryptophan hydroxylase (TRH), Tubulin Beta 3 Class III (TUBB3), TUC protein, tyrosine hydroxylase (TH), vanilloid receptor like protein (VRL), vesicular GABA transporter (VGAT), vesicular glutamate transporter (VGLUT) and/or Vimentin.

7. The method of claim 1, wherein the NSCs, neuron precursor cells or neurons or the PSCs are human.

8. The method of claim 1, further comprising treating the cells with guggulsterone to produce a dopaminergic (DA) neuron.

9. The method of claim 8, further comprising identifying at least one molecular marker on the DA neuron.

10. The method of claim 9, wherein the at least one molecular marker are is selected from the group consisting of neuron specific class III beta-tubulin (TUJ1), TH, FOXA2, nuclear receptor related 1 (Nurr-1), G-protein-regulated inward-rectifier potassium channel 2 (Girk2), microtubule-associated protein tau (MAPT), synaptotagmin 4 (SYT4), forkhead box protein A1 (FOXA1), DDC protein (DDC), Achaete-scute homolog 1 (ASCL1), PTEN-induced kinase I (PINK1), Paired box protein Pax-5 (PAX5), homeobox transcription factor I-beta (LMX1B), Pituitary homeobox 3 (PITX3), LIM homeobox transcription factor 1 alpha (LMXA1), Engrailed Homeobox 1 (EN1), Paired box protein Pax-2 (PAX2), Trefoil factor 3 (TFF3), pituitary homeobox 2 (PITX2), DCX, MAP2, pituitary homeobox 1 (PITX1) and vesicular monoamine transporter 2 (VMAT2).

* * * * *